(12) United States Patent
Messenger

(10) Patent No.: US 9,216,934 B1
(45) Date of Patent: Dec. 22, 2015

(54) SYSTEM AND METHOD FOR PH CONTROL OF LEAN MEG PRODUCT FROM MEG REGENERATION AND RECLAMATION PACKAGES

(71) Applicant: Cameron Solutions, Inc., Houston, TX (US)

(72) Inventor: Brian E. Messenger, Hook (GB)

(73) Assignee: Cameron Solutions, Inc., Houston, TX (US)

( * ) Notice: Subject to any disclaimer, the term of this patent is extended or adjusted under 35 U.S.C. 154(b) by 0 days.

(21) Appl. No.: 14/500,295

(22) Filed: Sep. 29, 2014

(51) Int. Cl.
*C07C 31/20* (2006.01)
*C09K 8/52* (2006.01)
*B01J 19/24* (2006.01)
*C09K 109/00* (2006.01)

(52) U.S. Cl.
CPC ............... *C07C 31/202* (2013.01); *B01J 19/24* (2013.01); *C09K 8/52* (2013.01); *B01J 2219/24* (2013.01); *C09K 2109/00* (2013.01); *C09K 2208/22* (2013.01)

(58) Field of Classification Search
CPC .......................... C09K 2109/00; C09K 2208/22
See application file for complete search history.

(56) References Cited

U.S. PATENT DOCUMENTS

2012/0018293 A1* 1/2012 Kaasa et al. ................... 203/18

OTHER PUBLICATIONS

Database CAPLUS in STN, Acc. No. 2012:1862384, Kaasa, WO 2012171554 A1 (Dec. 20, 2012) (abstract).*
Database CAPLUS in STN, Acc. No. 2013:1473466, Baraka-Lokmane et al., WIT Transactions on Engineering Sciences (2013), 79 (Computational Methods in Multiphase Flow VII), pp. 511-522 (abstract).*

* cited by examiner

*Primary Examiner* — Brian J Davis
(74) *Attorney, Agent, or Firm* — Gable Gotwals

(57) ABSTRACT

A lean MEG stream having a first pH level is contacted with a CO2-rich gas stream to yield a lean MEG product having a second different and lower pH level preferably in a range of 6.5 to 7.0. The system and method can be readily incorporated into a slipstream MEG recovery package, with a source of the lean MEG stream being a MEG regeneration section of the package. The $CO_2$-rich gas could be a vented $CO_2$ stream from the MEG reclamation section of the package. Unlike hydrochloric and acetic acid overdosing, $CO_2$ overdosing of the lean MEG stream does not lead to rapid acidification of the lean MEG product to be stored or injected.

10 Claims, 3 Drawing Sheets

SYSTEM AND METHOD FOR PH CONTROL OF LEAN MEG PRODUCT FROM MEG REGENERATION AND RECLAMATION PACKAGES

BACKGROUND OF THE INVENTION

Slipstream MEG recovery packages use a regeneration section to remove water from an incoming rich MEG feed stream and produce a lean MEG stream. A portion of this lean MEG stream is routed to a reclamation unit or section where the salt component is removed to yield a salt-free, pH neutral, lean MEG stream. This salt-free lean MEG stream is then blended with the remaining lean MEG stream to produce a lean MEG product having up to 3 wt % dissolved salts and available for re-injection into the gas production line as hydrate inhibitor.

For gas fields where significant quantities of calcium and other divalent cations are present in the formation water, a calcium removal unit or section is located upstream of the regeneration section. The calcium is removed from the rich MEG stream by elevating the pH through the addition of sodium or potassium carbonates, hydroxides, or some combination thereof. The lean MEG exits the calcium removal section with an elevated pH, typically above 9.5.

Because carbonate and hydroxide are often added in excess of the required stoichiometric quantity, un-reacted carbonate and hydroxide is carried through the regeneration system and into the lean MEG product. Removal of water from the rich MEG in the regeneration section further elevates the pH of the lean MEG product sent for re injection to above 10. Mixing this high pH lean MEG with the calcium-rich formation water in the gas production pipeline can lead to increased scaling of the pipeline by precipitation of, for example, calcium carbonate.

Therefore, a need exists to reduce the pH of the lean MEG product prior to injection and, in turn, mitigate pipeline scaling. Acidification of the lean MEG with hydrochloric acid (HCl) is an option but overdosing with hydrochloric acid can lead to rapid reduction in pH to levels at which corrosion of carbon steel pipework and vessels may occur.

SUMMARY OF THE INVENTION

A lean MEG stream having a first pH level (e.g., pH>9.5) is contacted with a $CO_2$-rich gas stream to yield a lean MEG product having a second different pH level preferably in a range of 6.5 to 7.0. The $CO_2$-rich gas could be a vented $CO_2$ stream from a MEG reclamation unit.

Carbon dioxide is preferred to hydrochloric acid (HCl) and acetic acid ($CH_3CO_2H$) for pH control because overdosing with $CO_2$—i.e., adding it in excess of the required stoichiometric quantity—does not lead to the significant reduction in pH observed with hydrochloric acid or the accumulation of acetates observed with acetic acid.

Objectives of this invention include providing a system and method that reduces the pH of lean MEG product prior to injection, mitigates the potential for pipeline scaling, does not make use of dosing with organic or inorganic acids to control the pH of the lean MEG product, is less sensitive to overdosing conditions than those organic and inorganic acids, and does not cause rapid reduction in pH levels when an overdose condition occurs.

ELEMENTS AND NUMBERING USED IN THE DRAWINGS

Figure 1:
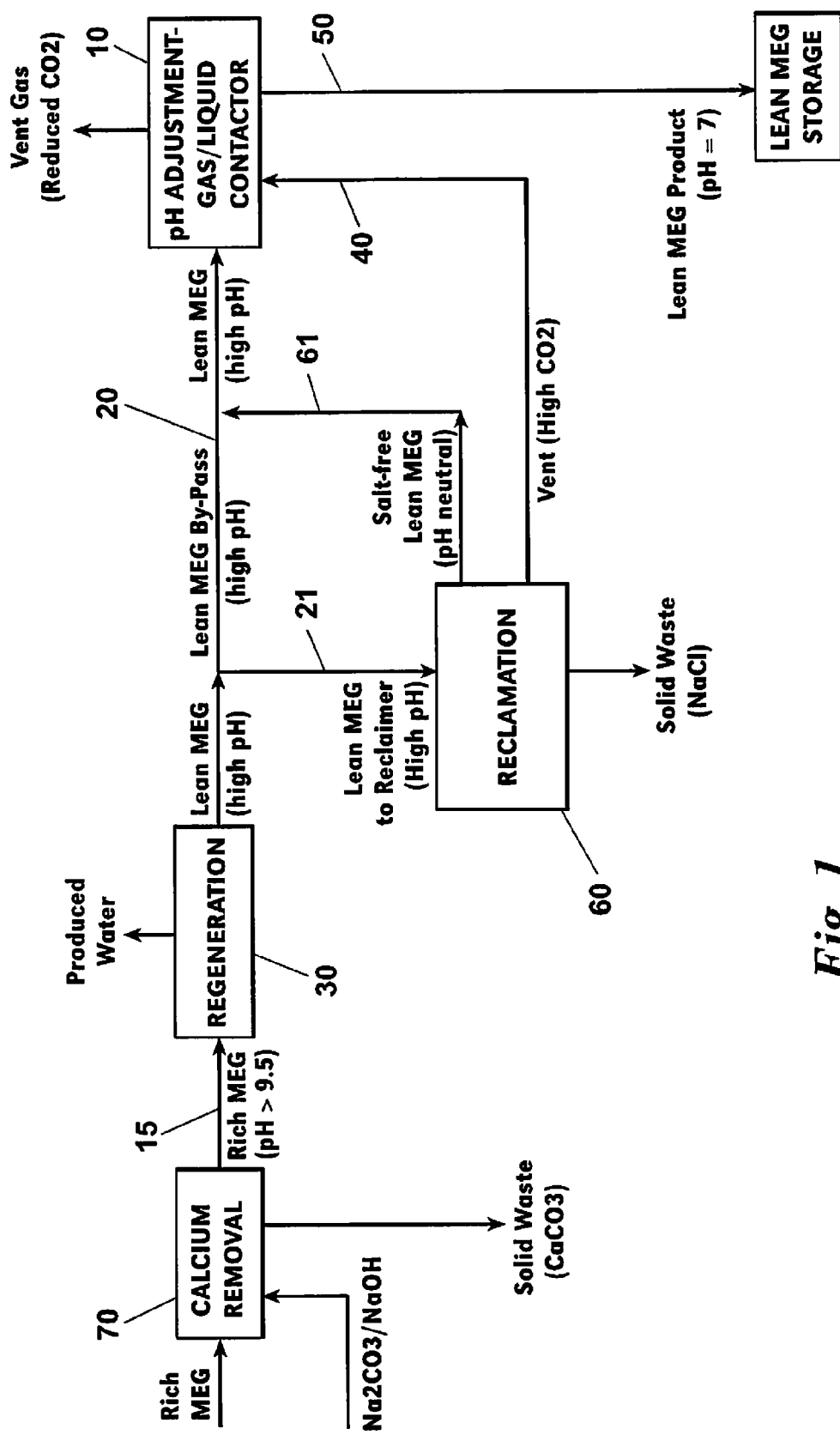
FIG. 1 is a schematic of a preferred embodiment of a system and method of this invention. A vessel located downstream of a MEG regeneration section receives a high pH lean MEG stream and allows the steam to come into contact with a $CO_2$-rich gas.

10 Vessel
15 Rich MEG steam
20 Lean MEG stream
21 Portion of lean MEG stream 20
30 MEG regeneration unit or section
40 $CO_2$-rich gas 40
50 Lean MEG product exiting 10
60 MEG reclamation unit or section
61 Salt-free lean MEG stream
70 Calcium removal unit or section

DETAILED DESCRIPTION OF THE PREFERRED EMBODIMENTS

Referring to FIG. 1, a preferred embodiment of a system and method for adjusting a pH level of a lean MEG steam includes a vessel 10 which receives a lean MEG stream 20 from a lean MEG source such as a regeneration unit or section 30 of a slipstream MEG recovery package. Typically, stream 20 has a pH level above 9.5, as does rich MEG stream 15 upstream of the regeneration section 30. Within vessel 10, this high pH lean MEG stream 20 comes into contact with a $CO_2$-rich gas 40 (i.e., greater than 50% $CO_2$ content). Vessel 10 can be a contactor vessel of a kind known in the art.

The $CO_2$ in gas 40 forms acidic solutions when dissolved in the MEG-water mixture of stream 20, thereby reducing the pH. A lean MEG product 50 having a second lower pH exits the vessel 10. Preferably, product 50 has a pH level in a range of 6.5 to 7. No inorganic acids such as HCl or organic acids such as acetic or citric acid is required for reducing the pH to this level.

The $CO_2$-rich gas 40 can be from any source preferable but is more preferably a vent stream from a reclamation unit or section 60 of the slipstream MEG recovery package. Similar to MEG regeneration section 30, MEG reclamation section 60 is of a kind well-known in the art.

A salt-free lean MEG stream 61 which exits the reclamation section 60 can be mixed with the lean MEG stream 20 prior to stream 20 entering vessel 10. Additionally, a portion 21 of the lean MEG stream 20 which exits the regeneration section 30 can be routed to the reclamation unit 60.

In slipstream MEG recovery packages that make use of a calcium removal unit or section 70 upstream of the regeneration unit 30, excess carbonate that finds its way into the reclamation section 60 degrades to form $CO_2$ (and hydroxide) under the elevated temperature, low pressure regime of a flash separator (not shown).

Figure 2:
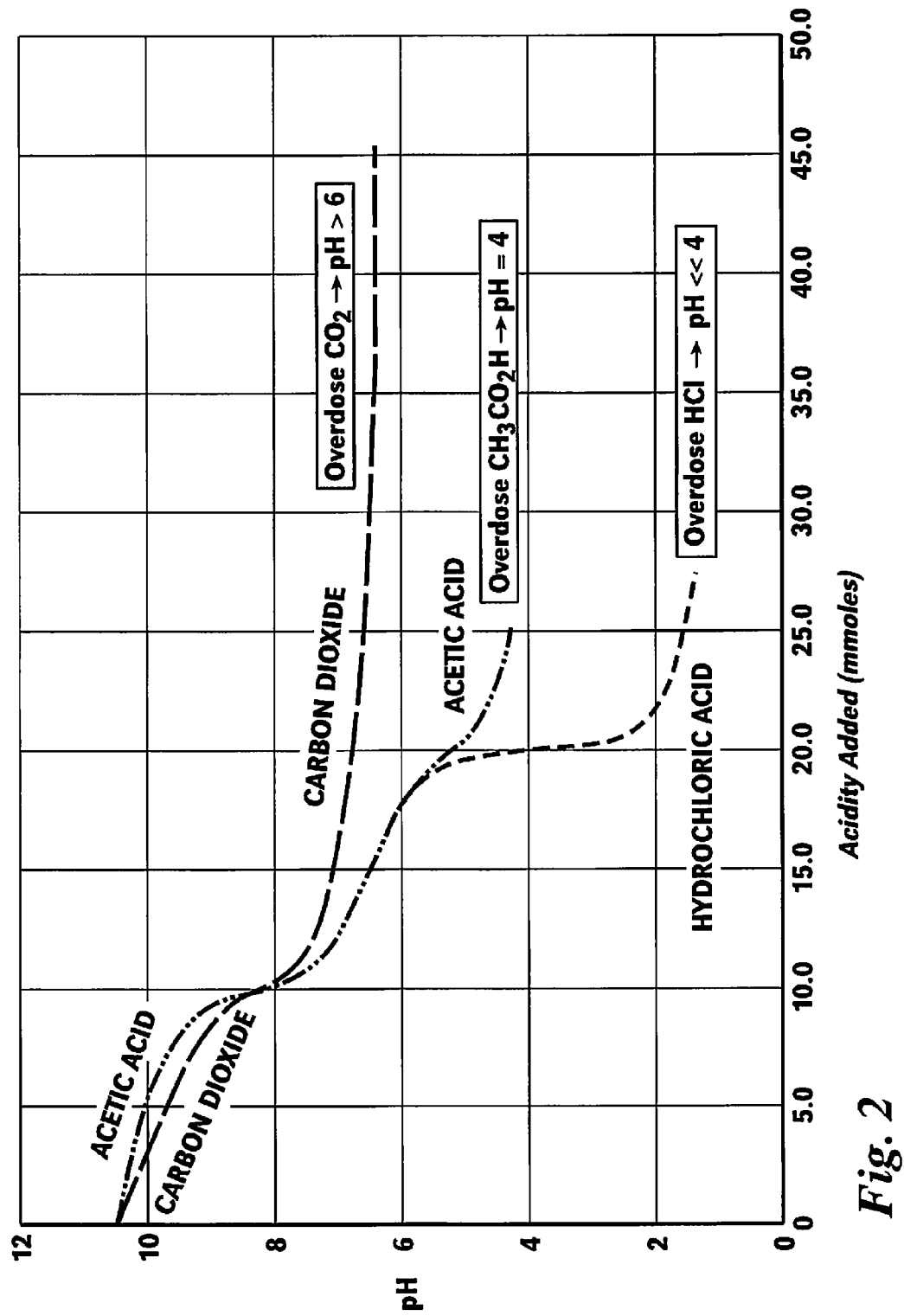
FIG. 2 is a graph illustrating a lean MEG stream with alkalinity present as sodium carbonate as the stream is treated with $CO_2$, acetic acid, and hydrochloric acid.
Figure 3:
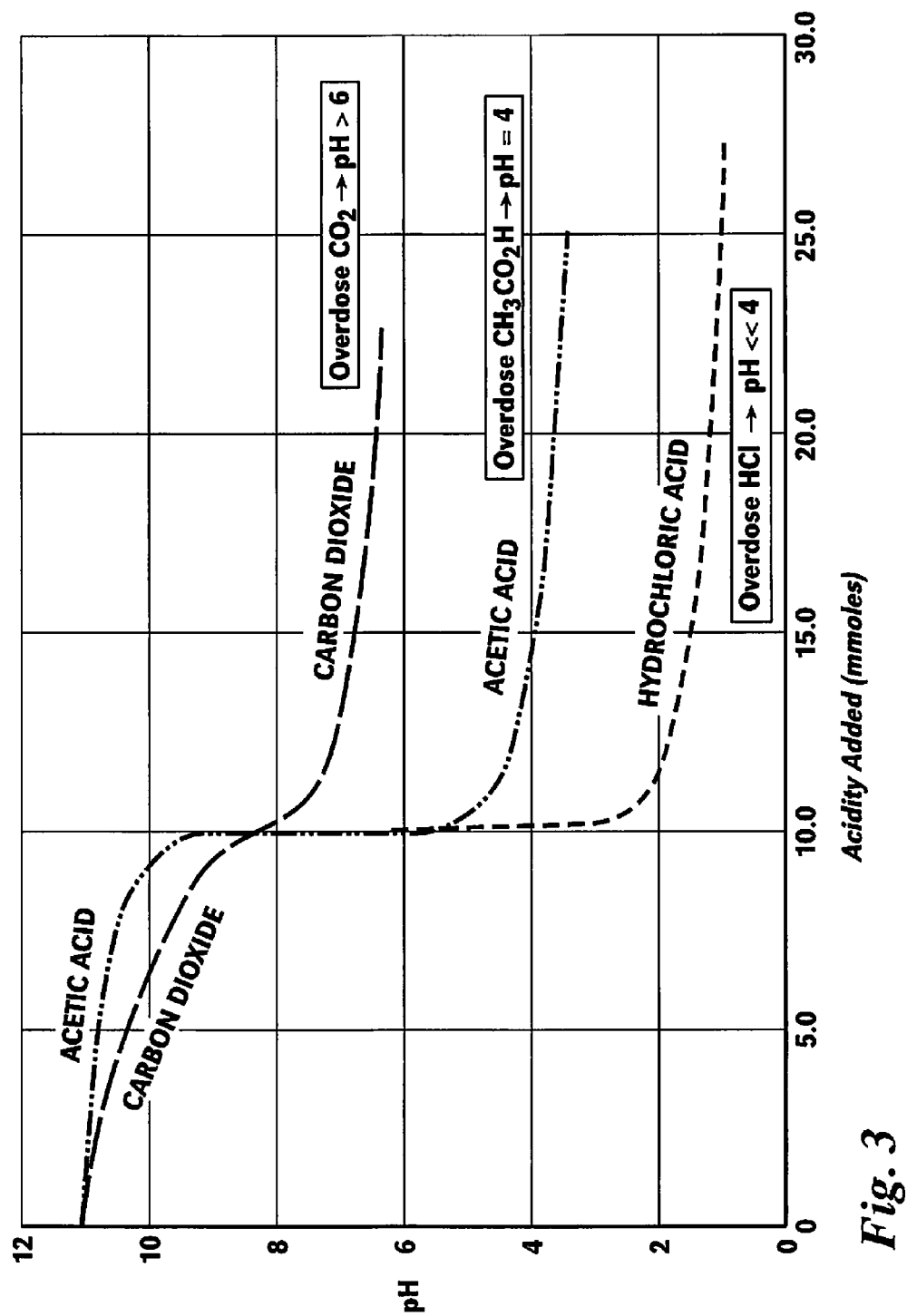
FIG. 3 is a graph illustrating a lean MEG stream with alkalinity present as sodium hydroxide as the stream is treated with $CO_2$, acetic acid, and hydrochloric acid.

Referring to FIGS. 2 and 3, unlike hydrochloric and acetic acid overdosing, $CO_2$ overdosing within vessel 10 does not lead to rapid acidification of the lean MEG product 50. In a $CO_2$ overdosing condition, the pH level remains above 6 whereas in an acetic acid and hydrochloric acid overdosing condition the pH level falls below 4 and 2 respectively. Therefore, the system and method of this invention is less sensitive to overdosing conditions than prior art methods.

As mentioned above, acidification with $CO_2$ removes the risk which occurs with inorganic acids (HCl) and the absence of carboxylates (acetate), namely, overdosing to the point of potentially damaging pH levels. In addition, carboxylates are highly soluble in MEG and are difficult to remove once added to the MEG system. The accumulation of carboxylates can lead to operational problems as the density and viscosity of the MEG increases with increasing carboxylate content. Hydrochloric acid converts readily to salt plus water; carbon dioxide converts to bicarbonate which is much more easily managed in the MEG system than carboxylates. Although the $CO_2$ reduces the pH, the 'alkalinity' (OH— plus $HCO_3$— plus $CO_2$) is not reduced.

To examine the "scaling" potential for the system and method, the following software simulation was run employing OLI Analyzer v 9.1.5 (OLI Systems, Inc., Cedar Knolls, N.J.).

Starting Solution:

90 wt % MEG (on salt-free basis) at 40° C. containing 30,000 $mg/kg_{solvent}$ sodium chloride, 250 $mg/kg_{solvent}$ of sodium carbonate and 25 $mg/kg_{solvent}$ of sodium hydroxide. The pH of this mixture was 10.053 or about 10 (see Table 1, col. A, below).

Acidification:

The MEG solution was neutralized to pH=7.0 and to pH=6.5 using HCl acetic acid and $CO_2$. Quantities of HCl, $CH_3CO_2H$ and $CO_2$ added are shown in Table 1, rows 12-14, below.

Scaling Test:

Scaling potential of the acidified solutions was determined by adding in separate simulations $MgCl_2$, $CaCl_2$, $FeCl_2$, $SrCl_2$ and $BaCl_2$ to the lean MEG solutions at the quantities shown in Table 1, rows 19-23.

equivalent scaling point with carbon dioxide occurs at 250 g, less than that for HCl or acetic acid but a considerable improvement on the 1.4 g for the untreated sample.

Similar trends are observed for the other divalent cations (Fe, Sr, Ba) although some are more insoluble than others. Iron, in particular, tends to precipitate out readily. At pH=6.5 (col. E-G) the trends agree with those shown at pH=7.0 (col. B-D), i.e. precipitation of divalent cations (Ca, Fe, Sr, and Ba) from the lean MEG is inhibited by addition of $CO_2$ to the alkaline lean MEG mixture.

While preferred embodiments have been described, the invention is defined by the following claims and their full range of equivalency.

What is claimed:

1. A method of adjusting a pH level of a lean MEG stream, the method comprising the step of contacting a lean MEG stream with a $CO_2$-rich gas, the lean MEG stream having a first pH level before coming into contact with the $CO_2$-rich gas and, after coming into contact with the $CO_2$-rich gas, having a second different pH level.

2. A method according to claim 1 wherein an amount of the $CO_2$-rich gas is at least equal to a stoichiometric quantity effective for achieving a desired second lower pH level.

3. A method according to claim 1 wherein the amount of $CO_2$-rich gas exceeds the stoichiometric quantity.

4. A method according to claim 1 wherein the second different pH level is at least 6.

5. A method according to claim 4 wherein the second different pH level is 7.

6. A method according to claim 1 wherein a source of the $CO_2$-rich gas is a vented $CO_2$ stream from a MEG reclamation unit.

7. A method according to claim 1 wherein upstream of the vessel the lean MEG stream is mixed with a second lean MEG stream having a different pH level than the first pH level of the lean MEG stream.

TABLE 1

Software Simulation of Scaling Potential.

| 1 | | | A | B | C | D | E | F | G |
|---|---|---|---|---|---|---|---|---|---|
| 2 | | | | | | | | | |
| 3 | TEMP | | 40 | 40 | 40 | 40 | 40 | 40 | 40 |
| 4 | | | | | | | | | |
| 5 | H2O | g | 100,000 | 100,000 | 100,000 | 100,000 | 100,000 | 100,000 | 100,000 |
| 6 | MEG | g | 900,000 | 900,000 | 900,000 | 900,000 | 900,000 | 900,000 | 900,000 |
| 7 | NaCl | g | 30,000 | 30,000 | 30,003 | 30,000 | 30,000 | 30,000 | 30,000 |
| 8 | Na2CO3 | g | 250 | 250 | 250 | 250 | 250 | 250 | 250 |
| 9 | NaOH | g | 25 | 25 | 25 | 25 | 25 | 25 | 25 |
| 10 | | | | | | | | | |
| 11 | ACIDIFICATION | | | | | | | | |
| 12 | HCl | g | 0 | 136 | — | — | 160 | — | — |
| 13 | CHCO2H | g | 0 | — | 228 | — | — | 279 | — |
| 14 | CO2 | g | 0 | — | — | 239 | — | — | 478 |
| 15 | | | | | | | | | |
| 16 | pH | | — | 10.05 | 7.01 | 7.01 | 7.01 | 6.50 | 6.50 | 6.50 |
| 17 | | | | | | | | | |
| 18 | SCALING TEST POST ACIDIFICATION | | | | | | | | |
| 19 | MgCl2 for Mg precipitation as Mg(OH)2 | g | | | | | | | |
| 20 | CaCl2 for Ca precipitation as CaCO3 | g | 1.4 | 840 | 880 | 250 | 4300 | 5300 | 800 |
| 21 | FeCl2 for Fe precipitation as FeCO3 | g | 0.1 | 1.5 | 1.7 | 0.8 | 6.7 | 7.7 | 2.4 |
| 22 | SrCl2 for Sr precipitation as SrCO3 | g | 0.5 | 650 | 660 | 200 | 3900 | 3950 | 620 |
| 23 | BaCl2 for Ba precipitation as BaCO3 | g | 0.2 | 7 | 13.7 | 2.1 | 35 | 80 | 6.3 |

Results:

For the starting solution (col. A, pH=10.0) precipitation of divalent cations as carbonate occurs on addition of 1.4 g of $CaCl_2$. After acidification to pH 7.0 with HCl, the quantity of calcium chloride added before precipitation of $CaCO_3$ increases to 840 g from 1.4 g. The effect with acetic acid is similar with precipitation starting at 880 g of $CaCl_2$. The 8. A method according to claim 7 wherein a source of the second lean MEG stream is a MEG reclamation unit.

9. A method according to claim 7 wherein the second lean MEG stream has a pH level of 7.

10. A method according to claim 1 wherein a source of the lean MEG stream is a MEG regeneration unit.

* * * * *